United States Patent
Sauer et al.

(10) Patent No.: US 8,688,204 B2
(45) Date of Patent: Apr. 1, 2014

(54) THERAPY DELIVERY FOR IDENTIFIED TACHYARRHYTHMIA EPISODE TYPES

(75) Inventors: William H. Sauer, Denver, CO (US); Shelley M. Cazares, Washington, DC (US); Dan Li, Shoreview, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 111 days.

(21) Appl. No.: 13/104,439

(22) Filed: May 10, 2011

(65) Prior Publication Data

US 2011/0218449 A1  Sep. 8, 2011

Related U.S. Application Data

(63) Continuation of application No. 11/715,128, filed on Mar. 7, 2007, now Pat. No. 7,941,208.

(60) Provisional application No. 60/861,594, filed on Nov. 29, 2006.

(51) Int. Cl.
*A61B 5/04* (2006.01)

(52) U.S. Cl.
USPC ............ 600/518; 607/14; 606/42; 600/508

(58) Field of Classification Search
USPC .................. 600/508, 509, 515–518, 510; 606/41.42; 607/14.27
See application file for complete search history.

(56) References Cited

U.S. PATENT DOCUMENTS

| | | | |
|---|---|---|---|
| 4,550,221 A | 10/1985 | Mabusth | |
| 4,686,332 A | 8/1987 | Greanias et al. | |
| 5,224,486 A | 7/1993 | Leman et al. | |
| 5,231,990 A | 8/1993 | Gauglitz | |
| 5,271,411 A | 12/1993 | Ripley et al. | |
| 5,299,118 A | 3/1994 | Martens et al. | |
| 5,312,445 A | 5/1994 | Nappholz et al. | |
| 5,331,966 A | 7/1994 | Bennett et al. | |
| 5,342,402 A | 8/1994 | Olson et al. | |
| 5,350,410 A | 9/1994 | Kleks et al. | |

(Continued)

FOREIGN PATENT DOCUMENTS

| EP | 0560569 | 9/1993 |
|---|---|---|
| EP | 1038498 | 9/2000 |

(Continued)

OTHER PUBLICATIONS

File History for U.S. Appl. No. 12/545,364.

(Continued)

*Primary Examiner* — Christopher D Koharski
*Assistant Examiner* — Pamela M Bays
(74) *Attorney, Agent, or Firm* — Brooks, Cameron & Huebsch, PLLC

(57) ABSTRACT

Methods and systems for identifying tachyarrhythmia episode types and delivering therapy to mitigate the identified tachyarrhythmia episode types are described. Electrogram signals of cardiac activity are sensed and stored by an implantable cardiac device. Tachyarrhythmia episodes are detected and tachyarrhythmia episode types are identified based on characteristics of the electrogram signals. In preparation for performing ablation, a tachyarrhythmia episode is induced. The features of the induced tachyarrhythmia episode are compared to characteristics of the identified episode types. A similarity between the induced tachyarrhythmia episode and at least one of the episode types identified from the stored electrogram signals is indicated to facilitate performing the ablation.

19 Claims, 8 Drawing Sheets

(56) References Cited

U.S. PATENT DOCUMENTS

| | | | |
|---|---|---|---|
| 5,411,533 A | 5/1995 | Dubreuil et al. | |
| 5,431,693 A | 7/1995 | Schroeppel | |
| 5,443,485 A | 8/1995 | Housworth et al. | |
| 5,458,620 A | 10/1995 | Adams et al. | |
| 5,605,158 A | 2/1997 | Snell | |
| 5,620,466 A | 4/1997 | Haefner et al. | |
| 5,626,620 A | 5/1997 | Kieval et al. | |
| 5,662,688 A | 9/1997 | Haefner et al. | |
| 5,674,254 A | 10/1997 | van Krieken | |
| 5,683,431 A | 11/1997 | Wang | |
| 5,697,959 A | 12/1997 | Poore | |
| 5,704,365 A | 1/1998 | Albrecht et al. | |
| 5,722,416 A | 3/1998 | Swanson et al. | |
| 5,735,882 A | 4/1998 | Rottenberg et al. | |
| 5,755,737 A * | 5/1998 | Prieve et al. | 607/4 |
| 5,779,645 A | 7/1998 | Olson | |
| 5,803,084 A | 9/1998 | Olson | |
| 5,836,971 A | 11/1998 | Starkweather | |
| 5,844,506 A | 12/1998 | Binstead | |
| 5,861,013 A | 1/1999 | Peck et al. | |
| 5,871,512 A | 2/1999 | Hemming et al. | |
| 5,873,897 A | 2/1999 | Armstrong et al. | |
| 5,873,898 A | 2/1999 | Hemming et al. | |
| 5,882,352 A | 3/1999 | Duncan et al. | |
| 6,091,990 A | 7/2000 | Hsu et al. | |
| 6,101,416 A | 8/2000 | Sloman | |
| 6,115,628 A | 9/2000 | Stadler et al. | |
| 6,134,473 A | 10/2000 | Hemming et al. | |
| 6,147,680 A | 11/2000 | Tareev | |
| 6,148,230 A | 11/2000 | KenKnight | |
| 6,175,766 B1 | 1/2001 | Bornzin et al. | |
| 6,230,055 B1 | 5/2001 | Sun et al. | |
| 6,253,102 B1 | 6/2001 | Hsu et al. | |
| 6,266,554 B1 | 7/2001 | Hsu et al. | |
| 6,267,778 B1 | 7/2001 | Cohen | |
| 6,301,503 B1 | 10/2001 | Hsu et al. | |
| 6,324,421 B1 | 11/2001 | Stadler et al. | |
| 6,324,427 B1 | 11/2001 | Florio | |
| 6,393,316 B1 | 5/2002 | Gillberg et al. | |
| 6,409,675 B1 | 6/2002 | Turcott | |
| 6,418,340 B1 | 7/2002 | Conley et al. | |
| 6,438,409 B1 | 8/2002 | Malik et al. | |
| 6,449,503 B1 | 9/2002 | Hsu | |
| 6,449,504 B1 | 9/2002 | Conley et al. | |
| 6,456,880 B1 | 9/2002 | Park et al. | |
| 6,491,639 B1 | 12/2002 | Turcott | |
| 6,496,715 B1 | 12/2002 | Lee et al. | |
| 6,499,504 B2 | 12/2002 | Conley et al. | |
| 6,505,067 B1 | 1/2003 | Lee et al. | |
| 6,512,940 B1 | 1/2003 | Brabec et al. | |
| 6,512,953 B2 | 1/2003 | Florio et al. | |
| 6,522,915 B1 | 2/2003 | Ceballos et al. | |
| 6,564,106 B2 | 5/2003 | Guck et al. | |
| 6,622,046 B2 | 9/2003 | Fraley et al. | |
| 6,625,490 B1 | 9/2003 | McClure et al. | |
| 6,631,290 B1 | 10/2003 | Guck et al. | |
| 6,690,967 B2 | 2/2004 | Meij | |
| 6,708,058 B2 | 3/2004 | Kim et al. | |
| 6,725,085 B2 | 4/2004 | Schwartzman et al. | |
| 6,754,523 B2 | 6/2004 | Toole | |
| 6,754,528 B2 | 6/2004 | Bardy et al. | |
| 6,760,615 B2 | 7/2004 | Ferek-Petric | |
| 6,766,190 B2 | 7/2004 | Ferek-Petric | |
| 6,768,923 B2 | 7/2004 | Ding et al. | |
| 6,856,835 B2 | 2/2005 | Bardy et al. | |
| 6,888,538 B2 | 5/2005 | Ely et al. | |
| 6,889,079 B2 | 5/2005 | Bocek et al. | |
| 6,904,315 B2 | 6/2005 | Panken et al. | |
| 6,925,330 B2 | 8/2005 | Kleine | |
| 6,950,702 B2 | 9/2005 | Sweeney | |
| 6,952,610 B2 | 10/2005 | Ostroff | |
| 6,973,350 B1 | 12/2005 | Levine et al. | |
| 6,988,003 B2 | 1/2006 | Bardy et al. | |
| 6,993,379 B1 | 1/2006 | Kroll | |
| 7,027,861 B2 | 4/2006 | Thompson | |
| 7,039,459 B2 | 5/2006 | Bardy | |
| 7,043,299 B2 | 5/2006 | Erlinger | |
| 7,065,400 B2 | 6/2006 | Schechter | |
| 7,065,410 B2 | 6/2006 | Bardy et al. | |
| 7,085,599 B2 | 8/2006 | Kim et al. | |
| 7,090,682 B2 | 8/2006 | Sanders et al. | |
| 7,092,754 B2 | 8/2006 | Bardy et al. | |
| 6,084,253 A1 | 9/2006 | Johnson et al. | |
| 7,120,495 B2 | 10/2006 | Bardy et al. | |
| 7,123,954 B2 * | 10/2006 | Narayan et al. | 600/518 |
| 7,146,206 B2 | 12/2006 | Glass et al. | |
| 7,194,309 B2 | 3/2007 | Ostroff et al. | |
| 7,228,173 B2 | 6/2007 | Cazares | |
| 7,236,819 B2 | 6/2007 | Brockway | |
| 7,242,978 B2 | 7/2007 | Cao | |
| 7,245,962 B2 | 7/2007 | Ciaccio et al. | |
| 7,263,399 B2 | 8/2007 | Carlson | |
| 7,277,754 B2 | 10/2007 | McCabe et al. | |
| 7,299,086 B2 | 11/2007 | McCabe et al. | |
| 7,457,664 B2 | 11/2008 | Zhang et al. | |
| 7,558,628 B2 | 7/2009 | Yonce et al. | |
| 7,580,741 B2 | 8/2009 | Cazares et al. | |
| 7,818,056 B2 | 10/2010 | Kim et al. | |
| 2002/0026220 A1 * | 2/2002 | Groenewegen et al. | 607/4 |
| 2002/0082658 A1 | 6/2002 | Heinrich et al. | |
| 2002/0095184 A1 | 7/2002 | Bardy et al. | |
| 2002/0107544 A1 | 8/2002 | Ostroff et al. | |
| 2002/0120311 A1 | 8/2002 | Lindh et al. | |
| 2003/0212436 A1 | 11/2003 | Brown | |
| 2004/0064159 A1 | 4/2004 | Hoijer et al. | |
| 2004/0215240 A1 | 10/2004 | Lovett et al. | |
| 2004/0230128 A1 | 11/2004 | Brockway et al. | |
| 2004/0239650 A1 | 12/2004 | Mackey | |
| 2004/0243014 A1 | 12/2004 | Lee et al. | |
| 2005/0004486 A1 | 1/2005 | Glass et al. | |
| 2005/0038478 A1 | 2/2005 | Klepfer et al. | |
| 2005/0137485 A1 | 6/2005 | Cao | |
| 2005/0288600 A1 | 12/2005 | Zhang et al. | |
| 2006/0047319 A1 | 3/2006 | Bruhns et al. | |
| 2006/0069322 A1 | 3/2006 | Zhang et al. | |
| 2006/0074331 A1 | 4/2006 | Kim et al. | |
| 2006/0111747 A1 | 5/2006 | Cazares et al. | |
| 2006/0111751 A1 | 5/2006 | Cazares | |
| 2006/0116593 A1 | 6/2006 | Zhang et al. | |
| 2006/0253043 A1 | 11/2006 | Zhang et al. | |
| 2006/0253044 A1 | 11/2006 | Zhang et al. | |
| 2006/0253164 A1 | 11/2006 | Zhang et al. | |
| 2008/0004665 A1 | 1/2008 | McCabe et al. | |
| 2008/0071182 A1 | 3/2008 | Cazares | |
| 2008/0125824 A1 | 5/2008 | Sauer | |
| 2009/0312813 A1 | 12/2009 | Cazares | |

FOREIGN PATENT DOCUMENTS

| | | |
|---|---|---|
| WO | WO9217240 | 10/1992 |
| WO | WO9220402 | 11/1992 |
| WO | WO0240097 | 5/2002 |
| WO | WO0247761 | 6/2002 |
| WO | WO03003905 | 1/2003 |
| WO | WO03028550 | 4/2003 |
| WO | WO2005058412 | 6/2005 |
| WO | WO2005089865 | 9/2005 |
| WO | WO2006065707 | 6/2006 |
| WO | WO2008005270 | 1/2008 |

OTHER PUBLICATIONS

File History for U.S. Appl. No. 11/715,128.
File History for U.S. Appl. No. 11/506,253.
Acar et al., "SVD-based on-line exercise ECG signal orthogonalization", IEEE Transactions on Biomedical Engineering, vol. 46, No. 3, (Mar. 1999). Abstract only.
Belouchrani et al., "Blind Source Separation Based on Time-Frequency Signal Representations", IEEE Transactions on Signal Processing, vol. 46, No. 11, pp. 2888-2897 (Nov. 1998).
Cohen et al. "Capture Management Efficacy in children and young adults with endocardial and unipolar epicardial systems", Europace, vol. 6, pp. 248-255 (2004).

(56) References Cited

OTHER PUBLICATIONS

Comon, "Independent component analysis, A new concept?", Signal Processing, vol. 36, No. 3, pp. 287-314, (Apr. 1994).

Gallois, et al., "Multi-Channel Analysis of the EEG Signals and Statistic Particularities for Epileptic Seizure Forecast", Second Joint EMBS/BMES Conference, pp. 208-215 (Oct. 23-26, 2002).

Gradaus et al., "Nonthoracotomy Implantable Cardioverter Defibrillator Placement in Children: Use of a Subcutaneous Array Leads and Abdominally Placed Implantable Cardioverter Defibrillators in Children", J. of Cardiovascular Electrophysiology, vol. 12, No. 3, pp. 356-360 (Mar. 2001).

Hyvärinen et al., "Independent Component Analysis: A Tutorial", Helsinski Univ. of Technology, (Apr. 1999).

Kolettis et al., "Submammary Implantation of a Cardioverter-Defibrillator with a Nonthoractomy Lead System", Am. Heart J., vol. 126, pp. 1222-1223 (Nov. 1993).

Krahn et al. "Recurrent syncope. Experience with an implantable loop record", Cardiol. Clin., vol. 15(2), (May 1997), pp. 316-326.

Leng et al., "Lead Configuration for Defibrillator Implantation in a Patient with Congenital Heart Disease and a Mechanical Prosthetic Tricuspid Valve", PACE, vol. 24, No. 8, pp. 1291-1292 (Aug. 2001).

Park et al., "Use of an Implantable Cardioverter Defibrillator in an Eight-Month-Old Infant with Ventricular Fibrillation Arising from a Myocardial Fibroma", PACE, vol. 22, No. 1, pp. 138-139 (Jan. 1999).

Rieta, et al., "Atrial Activity Extraction Based on Blind Source Separation as an Alternative to QRST Cancellation for Atrial Fibrillation Analysis", Computers in Cardiology, vol. 27, pp. 69-72 (2000).

Schuder et al., "Transthoracic Ventricular Defibrillation in the Dog with Truncated and Untruncated Exponential Stimuli", IEEE Transitions on Bio-Medical Engineering, vol. BME-18, No. 6, pp. 410-415, (Nov. 1971).

Schuder et al., "Experimental Ventricular Defibrillation with an Automatic and Completely Implanted System", Trans. Am. Soc. Artif. Int. Organs, vol. 16, pp. 207-212 (1970).

Schuder et al., "Ventricular Defibrillation in the Dog Using Implanted and Partially Implanted Electrode Systems", Am. J. of Cardiology, vol. 33, pp. 243-247 (Feb. 1974).

Smits et al., "Defibrillation Threshold (DFT) Model of a Fully Subcutaneous ICD System", Europace Supplements, vol. 2, at col. 778, p. B83, (Jun. 2001).

Splett et al. "Determination of Pacing Capture in Implantable Defibrillators: Benefit of Evoked Response Detection Using RV Coil to Can Vector," *PACE*, vol. 23, pp. 1645-1650, (2000).

Wilkoff BL, et al., Preventing Shocks after ICD Implantation: Can a Strategy of Standardized ICD Programming Match Physician Tailored? Late Breaking Trials, HRS 2005. No copy available.

Zarzoso et al., "Blind Separation of Independent Sources for Virtually Any Source Probability Density Function", IEEE Transactions on Signal Processing, vol. 47, No. 9, pp. 2419-2432 (Sep. 1999).

Zarzoso et al., "Noninvasive Fetal Electrocardiogram Extraction: Blind Separation Versus Adaptive Noise Cancellation", IEEE Transactions on Biomedical Engineering, vol. 48, No. 1, pp. 12-18 (Jan. 2001).

\* cited by examiner

THERAPY DELIVERY FOR IDENTIFIED TACHYARRHYTHMIA EPISODE TYPES

RELATED APPLICATIONS

This application is a continuation of patent application Ser. No. 11/715,128, filed on Mar. 7, 2007, to issue as U.S. Pat. No. 7,941,208 on May 10, 2011, which claims the benefit of Provisional Patent Application Ser. No. 60/861,594, filed Nov. 29, 2006, to which priority is claimed under 35 U.S.C. §120 and 35 U.S.C. §119(e), respectively, and which are incorporated herein by reference in their entireties.

FIELD OF THE INVENTION

The present invention relates generally to cardiac devices and methods, and, more particularly, to identifying tachyarrhythmia episode types and delivering therapy to mitigate the identified tachyarrhythmia episode types.

BACKGROUND OF THE INVENTION

Proper cardiac function relies on the synchronized contractions of the heart at regular intervals. When the heart is functioning normally, synchronized cardiac contractions are initiated at the sinoatrial node and the heart is said to be operating in normal sinus rhythm. However, if contractions of the heart become irregular or uncoordinated, or if the contraction rate is too fast or too slow, the heart rhythm is described as arrhythmic. Cardiac arrhythmia may be caused, for example, by disease processes or from aberrant electrical conduction patterns occurring in the heart tissue. Cardiac arrhythmia impairs cardiac pumping efficiency and some types of cardiac arrhythmia can be life threatening.

A cardiac arrhythmia that originates in an atrial region of the heart is denoted a supraventricular tachyarrhythmia (SVT). Atrial fibrillation and atrial flutter are examples of SVT. Both conditions are characterized by rapid, uncoordinated contractions of the atria resulting in hemodynamically inefficient pumping action.

Another example of SVT is sinus tachycardia, which is an increased heart rate due to exercise or a quick emotional response. In contrast to atrial fibrillation and atrial flutter, sinus tachycardia is characterized by rapid, coordinated contractions of the atria resulting in hemodynamically efficient pumping action, compensating for the increased strain placed upon the body during exercise or quick emotional responses. Whereas atrial fibrillation and atrial flutter are "abnormal" (yet not lethal), sinus tachycardia is "normal" (and also not lethal).

Cardiac arrhythmias originating in a ventricular region of the heart are denoted ventricular tachyarrhythmias. Ventricular tachycardia (VT) is characterized by rapid ventricular contractions and can degenerate into ventricular fibrillation (VF).

Ventricular fibrillation produces extremely rapid, non-coordinated contractions of the ventricles. Ventricular fibrillation is fatal unless the heart is returned to sinus rhythm within minutes or even seconds.

Implantable cardiac devices, including pacemakers and implantable cardioverter/defibrillators (ICDs), and have been used to deliver effective treatment to patients with serious cardiac arrhythmias. Implantable cardiac devices may treat cardiac arrhythmias with a variety of tiered therapies. These tiered therapies range from delivering low energy pacing pulses timed to assist the heart in maintaining pumping efficiency to providing high-energy shocks to treat and/or terminate fibrillation. To effectively deliver these treatments, the cardiac device must first identify the type of arrhythmia that is occurring, after which appropriate therapy may be delivered to the heart.

Some tachyarrhythmias are caused by abnormal cardiac tissue that creates short circuits in the electrical conduction pathways of the heart. Ablation is a therapeutic procedure that destroys the abnormal tissue to prevent or reduce recurrence of these types of tachyarrhythmias. Ablation may be used in conjunction with an ICD to reduce the number of shocks delivered to the heart to terminate VT or VF.

Methods and systems that facilitate identification of the causes of tachyarrhythmia episodes aid in determining appropriate therapies to treat the disorders causing the episodes. The present invention fulfills these and other needs.

SUMMARY OF THE INVENTION

The present invention is directed to methods and systems for identifying tachyarrhythmia episode types and delivering therapy to mitigate the identified tachyarrhythmia episode types. One embodiment is directed to a method of operating a cardiac system. Electrogram signals of cardiac activity are sensed and stored by an implantable cardiac device. Tachyarrhythmia episodes are detected using the electrogram signals. Tachyarrhythmia episode types are identified based on characteristics of the stored electrogram signals. In preparation for performing ablation, a tachyarrhythmia episode is induced. The features of the induced tachyarrhythmia episode are compared to characteristics of the identified episode types. A similarity is indicated between the induced tachyarrhythmia episode and at least one of the episode types identified from the stored electrogram signals to facilitate performing the ablation.

The characteristics of the tachyarrhythmia episodes of each episode type are associated with a conduction pattern of the episode type. The characteristics may involve one or more morphological characteristics and/or one or more interval characteristics of the tachyarrhythmia episodes.

In a further approach, the number of tachyarrhythmia episodes associated with each episode type are counted and displayed. The episode types may be ranked, where the rank of an episode type corresponds to a tachyarrhythmia burden of the episode type. The criteria used for the ranking is user programmable.

Ablation may be performed to prevent or mitigate future occurrences of one or more of the identified episode types. Episode types identified from tachyarrhythmia episodes stored before ablation may be compared to episode types identified from tachyarrhythmia episodes stored after ablation to confirm success of the ablation.

The number of distinct episode types may be determined algorithmically by an implantable or patient-external device or may be determined by a human analyst. In one implementation, after arranging the episodes in an order, the human analyst may identify one or more boundary episodes between the episode types. The tachyarrhythmia episodes may be grouped into episode types based on the boundary episodes.

In one implementation, a far field electrogram signal and a near field electrogram signal are sensed and stored. The characteristics identifying tachyarrhythmia episode types comprise morphological characteristics determined using the far field signal and the near field signal. In another implementation, a plurality of far field electrogram signals and a plurality of near field electrogram signals are sensed and stored. The characteristics identifying tachyarrhythmia episode types are determined using at least one of the far field signals and at least one of the near field signals.

In another approach, exit sites of the identified episode types are determined using the electrogram signals.

Another embodiment of the invention is directed to a cardiac system. The system includes an implantable sensing system and memory configured to sense and store electrogram signals. A tachyarrhythmia detector detects tachyarrhythmia episodes using the electrogram signals and determines characteristics of the tachyarrhythmia episodes from the electrogram signals. A data processor identifies episode types based on the characteristics of the tachyarrhythmia episodes. The data processor also determines a similarity between a tachyarrhythmia episode induced in preparation for performing ablation and at least one identified episode type. A display presents information related to the similarity between the induced tachyarrhythmia episode and the at least one identified episode type to facilitate performing the ablation.

The characteristics used to identify the episode types may include morphological characteristics or interval characteristics of the electrogram signals. The data processor may be configured to determine a number of distinct episode types and/or may discriminate a first type of ventricular tachyarrhythmia episode from a second type of ventricular tachyarrhythmia episode.

According to various implementations, the data processor may count the tachyarrhythmia episodes of the various episode types and/or may rank the episode types according to the tachyarrhythmia burden of the episode types.

In some implementations, the sensing system includes a first pair of cardiac electrodes configured to sense a far field electrogram signal and a second pair of cardiac electrodes configured to sense a near field electrogram signal. The tachyarrhythmia detector determines the characteristics of the tachyarrhythmia episodes using the far field electrogram signal and the near field electrogram signal.

In some implementations, the sensing system includes a plurality of far field cardiac electrode pairs, each far field electrode pair configured to sense a far field electrogram signal, and a plurality of near field cardiac electrode pairs, each near field electrode pair configured to sense a near field electrogram signal. The tachyarrhythmia detector determines the characteristics of the tachyarrhythmia episodes using at least one of the plurality of far field electrogram signals and at least one of the plurality of near field electrogram signals.

The data processor may be further configured to determine an exit site of one or more of the episode types based on the sensed and stored electrogram signals and/or may identify the exit site through comparison of the characteristics associated with a particular episode type to electrogram signals of paced beats.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1A:
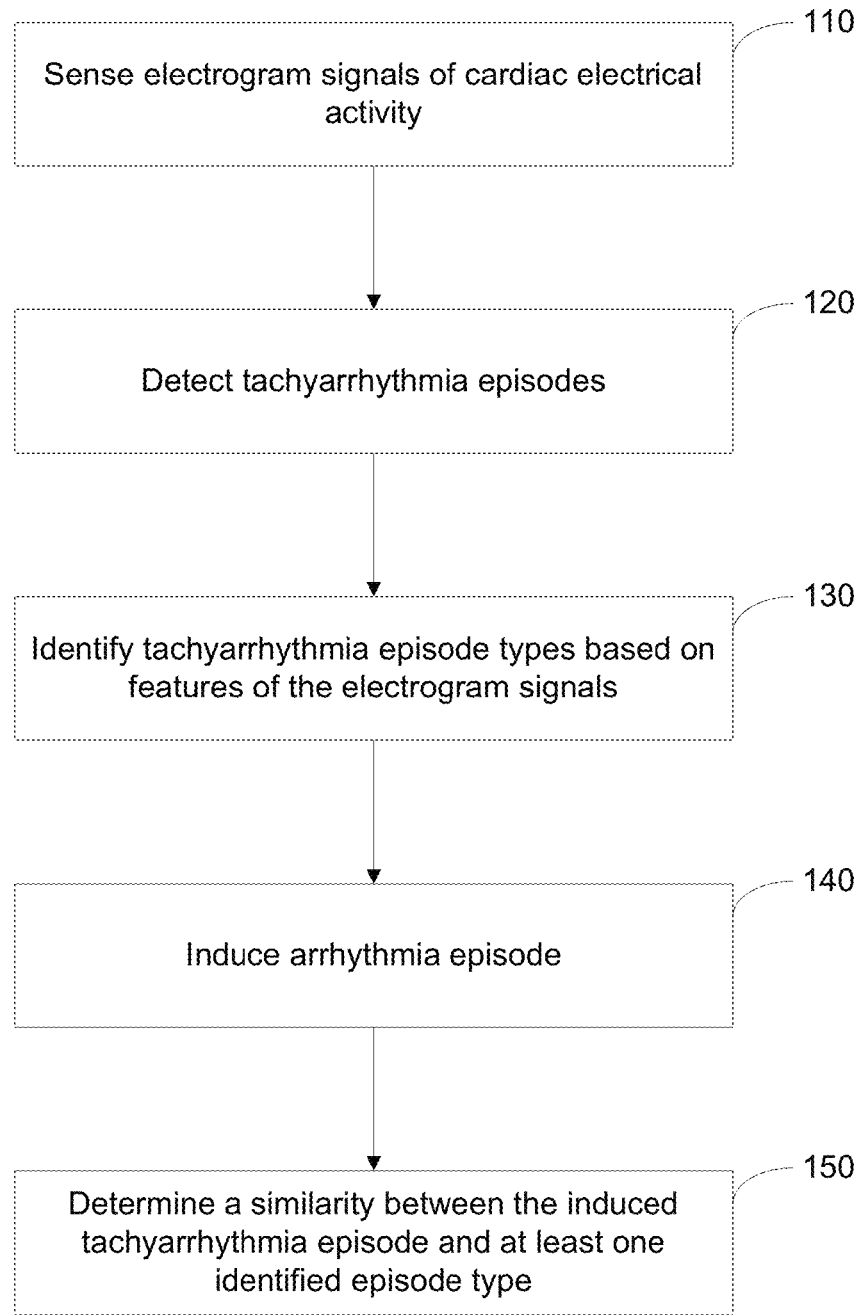
FIG. 1A is a diagram illustrating a process of determining or identifying tachyarrhythmia episode types and comparing identified episode types to an induced tachyarrhythmia episode in preparation for ablation in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings forming a part hereof, and in which are shown by way of illustration, various embodiments by which the invention may be practiced. It is to be understood that other embodiments may be utilized, and structural and functional changes may be made without departing from the scope of the present invention.

Tachyarrhythmias such as ventricular tachycardia (VT) or premature ventricular contractions (PVCs) can trigger ventricular fibrillation (VF) and sudden cardiac death. Implantable cardiac devices, e.g., implantable cardioverter/defibrillators (ICDs) treat VT and/or VF by delivering therapy in the form of anti-tachycardia pacing (ATP) and/or high energy defibrillation shocks. An interventional cardiac electrophysiologist can use catheter ablation techniques to ablate abnormal tissue causing PVCs or VT which may result in a reduced need for ICD therapy.

Some tachyarrhythmia episodes exhibit consistent morphology or interval patterns that may be discerned from the electrograms (EGMs) sensed during the episodes. Tachyarrhythmia episodes exhibiting consistent EGM patterns may be identified as belonging to particular episode types based on characteristics evident in the cardiac electrical signals of the tachyarrhythmia episodes. For example, the cardiac signals of tachyarrhythmia episodes of a first episode type exhibit representative morphological or interval characteristics that are distinct from the morphological or interval characteristics of tachyarrhythmia episodes of a second episode type. In one implementation, analysis of the electrogram signals by an implantable or patient-external device may be used to discriminate between distinct ventricular tachyarrhythmia episode types that exhibit consistent morphological or interval patterns. In addition, various types of ventricular tachyarrhythmias may be discriminated from episode types that are non-ventricular in origin, denoted herein as supraventricular tachyarrhythmias (SVTs).

Therapy to treat abnormal cardiac rhythms, including ablation, anti-tachyarrhythmia pacing (ATP), and/or defibrillation therapy, may be enhanced by identifying tachyarrhythmia episode types. For example, analysis of EGM signals collected by an ICD may be used to identify tachyarrhythmia episode types that historically have been experienced by the patient. Characteristics of an induced tachyarrhythmia episode may be compared to the identified episode types prior to ablation. Similarities between the induced tachyarrhythmia episode and the identified episode types may be used in determining or confirming ablation sites.

Episode types that are more problematic for the patient may include episode types that occur more frequently, are sustained, require therapy delivery for termination, are highly unstable, and/or that typically accelerate to VF. Embodiments of the invention are directed to methods and systems that determine the "tachyarrhythmia burden" as a way of ranking the tachyarrhythmia episodes types according to predetermined criteria. For example, the episode types may be ranked based on the number or frequency of occurrence of episode types. In some implementations, the episode types may be ranked based on factors such as the instability of the episode types, the amount of morphological disorganization of the episode type, the tendency of the episode type to accelerate to VF, the responsiveness of the episode type treatment such as ATP, and/or other factors.

One embodiment of the invention is illustrated in the diagram of FIG. 1A. An ICD includes electrodes disposed in appropriate locations in, on, or about the heart for sensing cardiac electrical activity. Via the electrodes and sensing circuitry disposed within the ICD housing, the device senses 110 electrogram (EGM) signals of cardiac electrical activity. The EGM signals may be stored in the ICD for a period of time and/or may be transmitted to a patient-external device via a telemetric link.

ICDs typically include cardiac electrodes that are in electrical contact with the myocardium and sense cardiac electrical signals that provide information about the depolarization status of the heart. Near field sensing yields signals that are most strongly representative of the activation signals that are present close to the site of an electrode pair.

Far field signals provide a more global view of the depolarization status of the heart than near field signals. For example, a sensed far field cardiac activation signal is effectively a superposition of a number of near field depolarization signals occurring within the heart that are associated with a cardiac contraction.

ICDs that include pacing capability typically include tip electrodes that are configured to make direct contact with the myocardium. Tip electrodes may be used for near field sensing of cardiac electrical signals. Far field sensing may be accomplished via various electrode pairs of an ICD, such as transvenous, endocardial, and/or epicardial electrodes (i.e., intrathoracic electrodes), and/or subcutaneous, non-intrathoracic electrodes, including can, header, and indifferent electrodes, and subcutaneous array or lead electrodes (i.e., non-intrathoracic electrodes). For example, electrode pairs suitable for far field sensing in an ICD may include RV-ring to RV-coil, RV-ring to SVC-coil, RV-ring to RA-ring, or may include sensing between two can electrodes, between a can electrode and an indifferent electrode, or between a can or indifferent electrode and a ring or coil electrode. ICDs capable of biventricular pacing provide additional near field and far field sensing capabilities. An electrode pair used for sensing cardiac electrical activity is referred to herein as a sensing vector. A sensing vector includes at least a pair of sensing electrodes, where each electrode of the pair may comprise multiple electrodes and/or multiple electrode elements used for sensing.

Returning now to FIG. 1A, near field and/or far field cardiac electrical signals are sensed by the ICD. Tachyarrhythmia episodes are detected 120 from the EGM signals. The EGM signals of the tachyarrhythmia episodes may be stored in the memory of the ICD, optionally along with data acquired from additional physiological or non-physiological sensors. The additional data may include information such as time and day of the episode, episode onset, episode duration, morphological organization associated with the episode, therapy delivered, therapy success, and/or other data.

Tachyarrhythmia episode types are identified 130 through analysis of the EGM signal features of the tachyarrhythmia episodes. Each episode type is associated with a certain morphology or interval pattern of the EGM signal, which in turn is indicative of a conduction pattern associated with the episode type. Each episode type detected by the device is given a label, e.g., VT001 or PVC001.

During pre-ablation mapping, tachyarrhythmia episodes are induced 140. Features of the induced tachyarrhythmia episodes are compared to the characteristic features of the identified episode types. The similarity between the induced episode and at least one identified episode type is determined 150. The similarity may be displayed or otherwise indicated to facilitate the ablation.

Figure 1B:
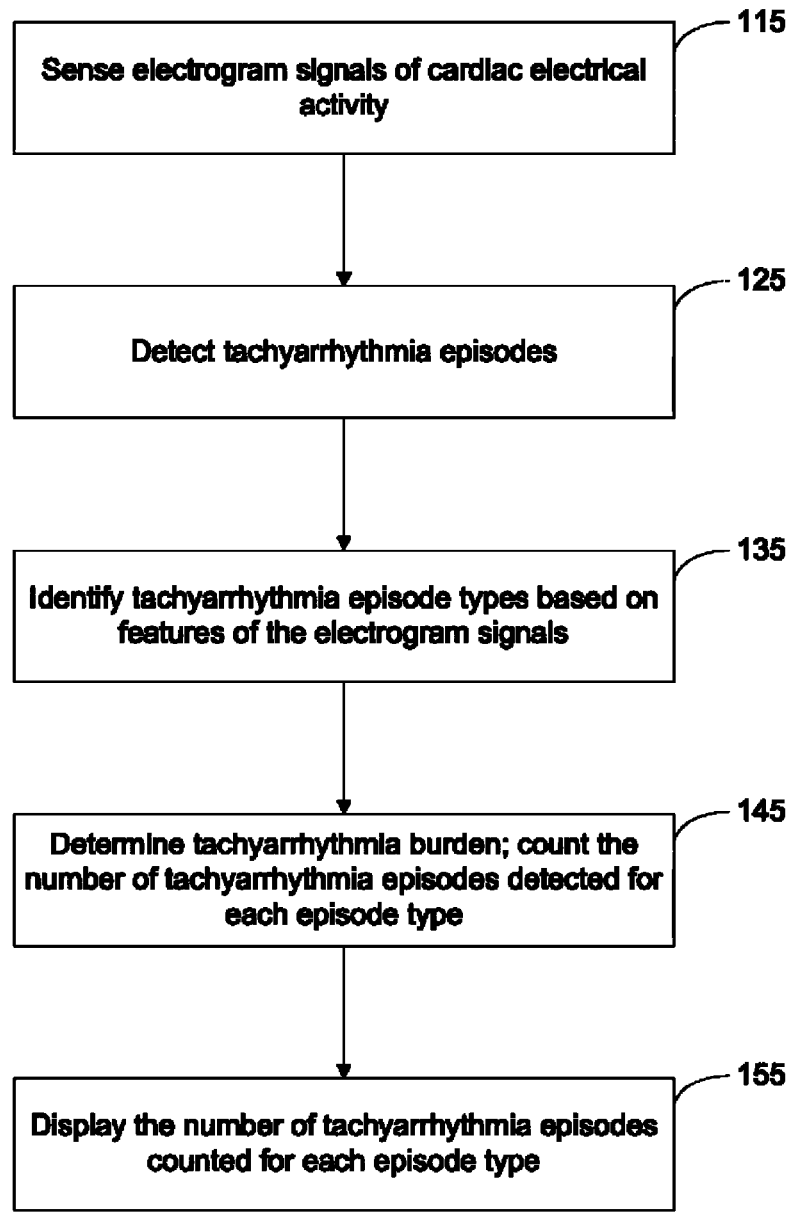
FIG. 1B is a diagram illustrating a process for identifying tachyarrhythmia episode types and determining a tachyarrhythmia burden of episode types in accordance with embodiments of the invention.

Another process in accordance with embodiments of the invention is illustrated in the diagram of FIG. 1B. Electrogram signals are sensed 115 and stored in an ICD. Tachyarrhythmia episodes are detected 125 from the stored electrogram signals. Tachyarrhythmia episode types are identified 135 through analysis of the EGM signal features of the tachyarrhythmia episodes. The tachyarrhythmia episodes associated with each episode type are counted 145. The numbers of tachyarrhythmia episodes associated with the episode types are displayed 155.

One approach to detecting tachyarrhythmia episodes and classifying episode types is based on sensed event intervals, e.g., the P-P, P-R, R-P, or R-R timing intervals, and/or the atrial heart rate compared to ventricular heart rate along with the stability of the intervals and/or the onset characteristics of the intervals. Event intervals and rates may be identified as they occur and are compared to preset criteria, which must be met in order to identify a particular tachyarrhythmia type. U.S. Pat. No. 5,342,402, which is incorporated herein by reference, describes an interval based tachyarrhythmia detection and classification system and method.

In other approaches, the morphology of the EGM signal of a representative beat of the tachyarrhythmia episode may be analyzed to detect tachyarrhythmia and to classify tachyarrhythmia episode types. For example, morphological features extracted from the EGM signals may be compared to a template including corresponding features representative of a particular type of tachyarrhythmia. The features extracted from the EGM signal may include the time coordinates of local maxima and minima points of the cardiac signal, for example. If the signal features are sufficiently similar to the template features, the tachyarrhythmia episode may be identified as the episode type represented by the template. Additional details related to extraction of features points from cardiac signals and the use of such feature points to discriminate between various cardiac rhythms is described in commonly owned U.S. Pat. Nos. 6,266,554 and 6,449,503 which are incorporated herein by reference.

In yet another embodiment, the electrogram signal characteristics used to identify tachyarrhythmia episode types are coefficients of Fourier or wavelet decomposition of a composite cardiac beat signal for the episode. In one implementation, the composite beat signal of an episode is transformed into a number of signal wavelet coefficients using a wavelet transform, such as a Haar wavelet transform. The higher amplitude signal wavelet coefficients are identified and used as discriminating features of the episode. Additional details regarding the use of wavelet transformation to extract wavelet coefficients of cardiac electrogram signals are described in U.S. Pat. No. 6,393,316 which is incorporated herein by reference.

In yet a further embodiment, the features of the electrograms used to classify tachyarrhythmia episode types include areas between sections of an EGM signal (which may be a composite signal) and a baseline. For example, a group of consecutive peaks having the largest cumulative peak values are determined from the EGM signal. Features of the peaks such as areas of each peak, are determined and used to discriminate between different types of tachyarrhythmia. Additional features used for discriminating episode types may comprise the polarity and/or position of the peak. Further discussion regarding the extraction of peak information for use as discriminating features of a cardiac EGM signal are discussed in U.S. Pat. No. 5,779,645 which is incorporated herein by reference.

In some configurations, the episode types are ranked and the rankings are displayed. For example, the rankings may be displayed along with the number of episodes counted for each episode type. Counting or ranking the episode types provides a physician with an assessment of the tachyarrhythmia burden associated with each episode type. Furthermore, identifying and/or ranking tachyarrhythmia episode types may be used to provide the electrophysiologist with a pre-ablation map of PVC or VT pattern "signatures" of frequently occurring or otherwise problematic tachyarrhythmia episode types.

One implementation in accordance with embodiments of the invention involves ranking episode types based on the number of times a tachyarrhythmia episode of a particular episode type occurs. For example, the episode types may be ranked according to the number of tachyarrhythmia episodes counted for each episode type. The episode type with the highest count is ranked as having the highest tachyarrhythmia burden. The episode type having the lowest count is ranked lowest.

In other implementations, information in addition to the EGM signals may be stored and linked to the episode types. The additional information may be used in ranking the episode types. In these implementations, the episode types may be ranked according to onset characteristics, stability characteristics, duration, success or failure of therapies used for treatment, or other characteristics. The characteristics used for ranking may be programmable.

By identifying and labeling specific episode types, the electrophysiologist will also be able to identify supraventricular tachyarrhythmias (SVTs) that may be conducted aberrantly. If not identified, supraventricular tachyarrhythmias, which have their own characteristics, may cause an inappropriate shock. Therefore, identification of an SVT based on characteristics of the EGM would result in therapy inhibition the next time this SVT occurs. Using this implementation, specific therapies, or withholding of nominally programmed therapies, can be programmed according to the tachyarrhythmia identified. For example, an SVT that is conducted aberrantly (i.e. unlike the stored sinus rhythm template) can be identified by the device which can be programmed to inhibit therapy for the episode type. Similarly, a specific VT can be programmed to be treated with anti-tachycardia pacing even if the rate identifies it as a tachyarrhythmia in the VF zone. Similarly, tailored therapy with specific ATP sequences using a specific left ventricular, right ventricular, or biventricular stimulation or immediate shock delivery, regardless or rate can be assigned to any type of tachyarrhythmia type observed.

Information provided by ranking the episode types may be used by an electrophysiologist in performing ablation to prevent future occurrences of certain episode types. For example, it may be desirable to perform ablation to eliminate one or more episode types associated with the highest tachyarrhythmia burden. In another implementation, ranking the tachyarrhythmia episode types may be used by a physician to adjust the programmable settings of an ICD to enhance electrical stimulation therapies delivered by the device, or may be used for other therapeutic or diagnostic purposes. Information about the tachyarrhythmia episodes, including the rankings of the tachyarrhythmia episodes before and after ablation is performed and/or before and after the ICD settings are adjusted, may be displayed and/or compared.

Figure 2:
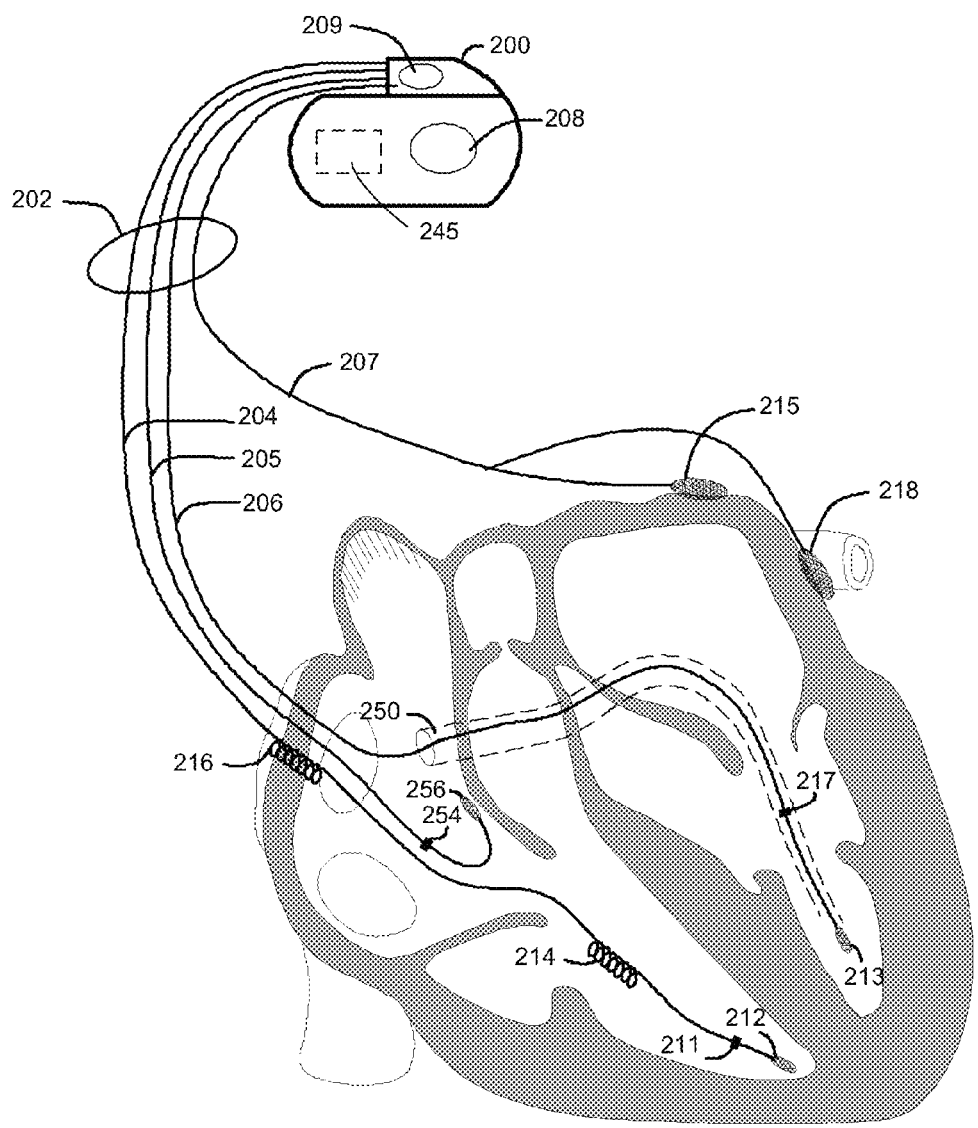
FIG. 2 shows an implantable cardiac device configured to acquire data related to cardiac episodes in accordance with embodiments of the invention.

Referring now to FIG. 2 of the drawings, there is shown an ICD configured to implement methods in accordance with various embodiments of the present invention. The ICD 200 in FIG. 2 includes pacemaker and defibrillator circuitry enclosed within a housing and coupled to a lead system 202. The housing and/or header of the device 200 may incorporate one or more can or indifferent electrodes 208, 209 used to provide electrical stimulation energy to the heart and/or to sense cardiac electrical activity. The ICD 200 may utilize all or a portion of the device housing as a can electrode 208 and/or may have multiple can electrodes disposed on the housing. The ICD 200 may include one or more indifferent electrodes 209 positioned, for example, on the header or the housing of the ICD 200.

The lead system 202 is used to sense cardiac electrical signals produced by the heart and to provide electrical energy to the heart under certain predetermined conditions to treat cardiac arrhythmias. The lead system 202 may include one or more electrodes used for pacing, sensing, and/or defibrillation. In the embodiment shown in FIG. 2, the lead system 202 includes an intracardiac right ventricular (RV) lead system 204, an intracardiac right atrial (RA) lead system 205, and an intracardiac left ventricular (LV) lead system 206. An extracardiac left atrial (LA) lead system 207 may optionally be employed.

The ICD 200 and lead system 202 illustrated in FIG. 2 may be configured for biventricular or biatrial sensing and/or pacing. The lead system 202 of FIG. 2 illustrates one embodiment that may be used in connection with the processes described herein. Other leads and/or electrodes may additionally or alternatively be used. For example, the lead system 202 may include multiple electrodes in one chamber configured for intrachamber pacing and sensing. In this configuration, the ICD 200 may pace and/or sense at multiple sites in one cardiac chamber via multiple electrodes within the chamber. This type of multisite pacing and sensing may be employed in one or more of the right atrium, left atrium, right ventricle or left ventricle. Multisite pacing in a chamber may be used for example, to increase the synchrony of cardiac contractions of the paced chamber.

As illustrated in FIG. 2, the lead system 202 may include one or more extracardiac leads 207 having electrodes 215, 218, e.g., epicardial electrodes, patch electrodes or other types of extracardiac electrodes positioned at locations outside the heart for sensing and pacing one or more heart chambers. In various configurations, the epicardial electrodes may be placed on or about the outside of the heart and/or may be embedded in the myocardium from the locations outside the heart.

The right ventricular lead system 204 illustrated in FIG. 2 includes an SVC-coil 216, an RV-coil 214, an RV-ring electrode 211, and an RV-tip electrode 212. The right ventricular lead system 204 extends through the right atrium and into the right ventricle. In particular, the RV-tip electrode 212, RV-ring electrode 211, and RV-coil electrode 214 are positioned at appropriate locations within the right ventricle for sensing right ventricular cardiac signals and delivering electrical stimulation pulses to the heart. The SVC-coil 216 is positioned at an appropriate location within the right atrium chamber of the heart or a major vein leading to the right atrial chamber.

In one configuration, the RV-tip electrode 212 referenced to the can electrode 208 may be used to implement unipolar pacing and/or near field sensing in the right ventricle. Bipolar pacing and/or sensing in the right ventricle may be implemented using the RV-tip 212 and RV-ring 211 electrodes. In yet another configuration, the RV-ring 211 electrode may optionally be omitted, and bipolar pacing and/or sensing may be accomplished using the RV-tip electrode 212 and the RV-coil 214, for example. The right ventricular lead system 204 may be configured as an integrated bipolar pace/shock lead. The RV-coil 214 and the SVC-coil 216 are defibrillation electrodes.

The left ventricular lead 206 includes an LV distal electrode 213 and an LV proximal electrode 217 located at appropriate locations in or about the left ventricle for pacing and/or sensing the left ventricle. The left ventricular lead 206 may be guided into the right atrium of the heart via the superior vena cava. From the right atrium, the left ventricular lead 206 may be deployed into the coronary sinus ostium, the opening of the coronary sinus 250. The lead 206 may be guided through the coronary sinus 250 to a coronary vein of the left ventricle. This vein is used as an access pathway for leads to reach the surfaces of the left ventricle which are not directly accessible from the right side of the heart. Lead placement for the left ventricular lead 206 may be achieved via subclavian vein access and a preformed guiding catheter for insertion of the LV electrodes 213, 217 adjacent to the left ventricle.

Unipolar pacing and/or near field sensing in the left ventricle may be implemented, for example, using the LV distal electrode 213 referenced to the can electrode 208. The LV distal electrode 213 and the LV proximal electrode 217 may be used together as bipolar sense and/or pace electrodes for the left ventricle. The lead system 202 in conjunction with the device 200 may provide bradycardia pacing therapy to maintain a hemodynamically sufficient heart rate. The left ventricular lead 206 and the right ventricular lead 204 and/or the right atrial lead and the left atrial lead may be used to provide cardiac resynchronization therapy such that the ventricles and/or atria of the heart are paced substantially simultaneously or in phased sequence separated by an interventricular or interatrial pacing delay, to provide enhanced cardiac pumping efficiency for patients suffering from congestive heart failure.

The right atrial lead 205 includes a RA-tip electrode 256 and an RA-ring electrode 254 positioned at appropriate locations in the right atrium for sensing and pacing the right atrium. In one configuration, the RA-tip 256 referenced to the can electrode 208, for example, may be used to provide unipolar pacing and/or sensing in the right atrium. In another configuration, the RA-tip electrode 256 and the RA-ring electrode 254 may be used for bipolar pacing and/or sensing.

The ICD 200 can be programmed to acquire the near field and/or far field cardiac signals sensed via electrodes 211-218, 254, 256, 208 and 209 during cardiac tachyarrhythmia episodes. Near field sensing vectors include, for example, the signals recorded from a tip electrode. Far field sensing vectors may include the bipolar signals recorded from the ring of a pacing lead to the device canister and/or defibrillation coils. The number of far field signals recorded is a function of the number of electrodes included in the system.

The device circuitry includes a memory 245 for storing cardiac signals and/or other data, including data related to tachyarrhythmia episodes. The ICD 200 also includes communication circuitry (not shown) to facilitate wireless communication with a patient-external device, such as a device programmer and/or remote server. The cardiac signals and/or other data may be acquired and stored in the ICD memory for a period of time. The stored signals and data may be downloaded periodically or on command to a remote system via the communications circuitry.

Although the ICD 200 is described as an implantable therapy device, the device that acquires the episode data need not be implantable and need not have therapy capability. For example, the principles of the invention are also applicable using a cardiac monitor that is patient-external and only acquires and optionally stores cardiac signals without delivering therapy.

Figure 3:
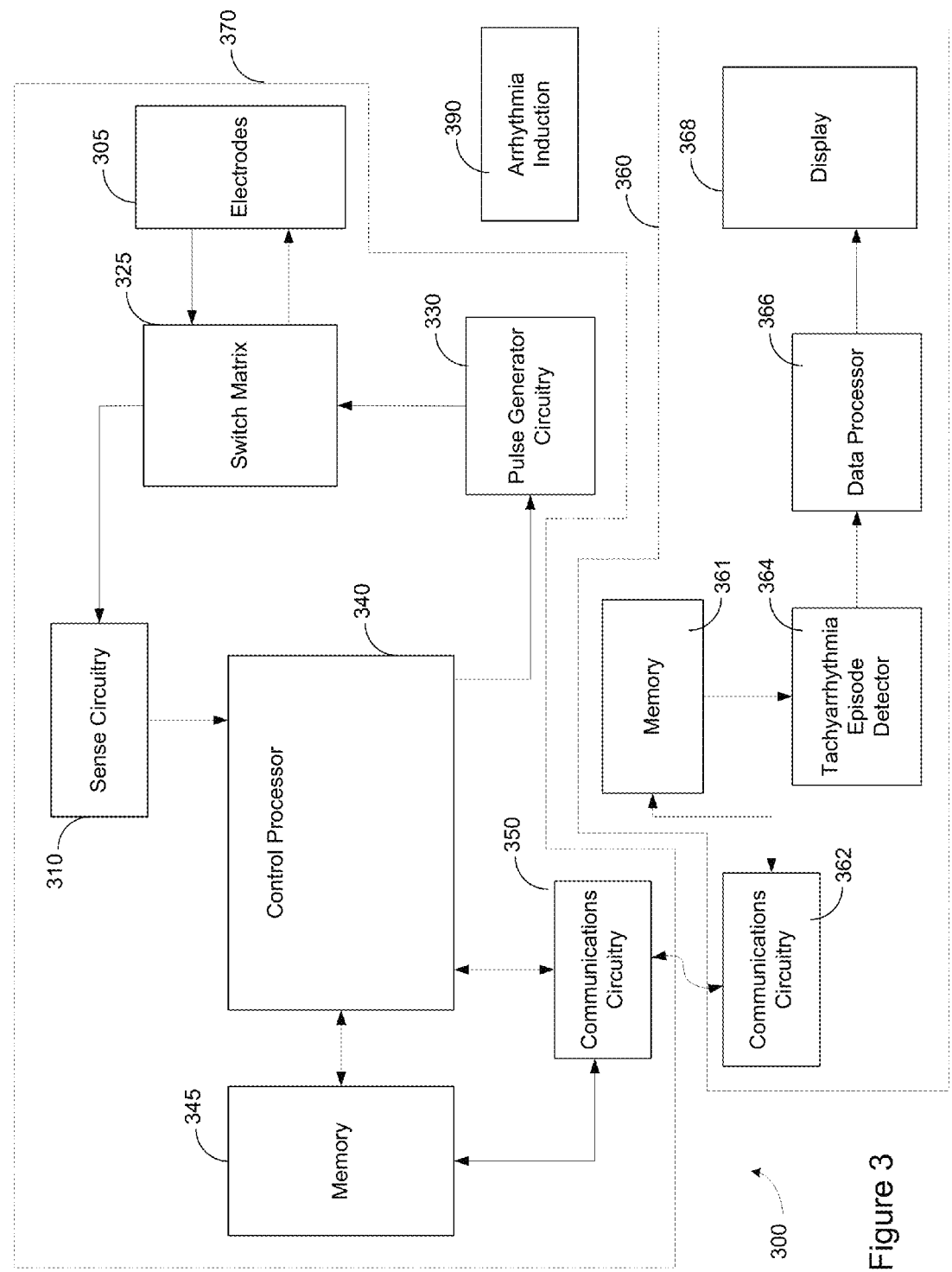
FIG. 3 depicts a block diagram of a system suitable for acquiring cardiac episode data, for identifying cardiac episodes, and for determining the tachyarrhythmia burden associated with the cardiac episodes in accordance with embodiments of the present invention.

Referring now to FIG. 3, there is shown a block diagram of a system suitable for identifying tachyarrhythmia episode types, determining similarities between induced tachyarrhythmia episodes and previously identified episode types. Components of the system 300 of FIG. 3 may operate to count tachyarrhythmia episodes and/or rank episode type in accordance with various embodiments of the invention. FIG. 3 shows a system 300 divided into functional blocks. It is understood by those skilled in the art that there exist many possible configurations in which these functional blocks can be arranged. The example depicted in FIG. 3 is one possible functional arrangement. Other arrangements are also possible. For example, more, fewer or different functional blocks may be used. Although the system depicted in FIG. 3 contemplates the use of programmable microprocessor-based logic circuits, other circuit implementations may be utilized. Further, the system 300 illustrates an implementation that includes implantable components 370 and patient-external components 360. It will be understood that in other implementations more, fewer or different components may be implemented as patient-external components and/or more, fewer or different components may be implemented as implantable components.

The system 300 includes implantable electrodes 305 coupled to sensing circuitry 310 through a switch matrix 325. The electrodes 305 may be disposed implantably at multiple locations within, on, or about the heart, may be disposed subcutaneously, e.g., on the surface of an implantable device housing, and/or may be arranged patient-externally on the surface of the patient's skin, as previously described. Various combinations of the electrodes coupled via the switch matrix 325 to the sensing circuitry 310 may be used to sense near field and/or far field cardiac electrical signals.

Control processor 340 may include circuitry for triggering data acquisition before, during and/or after the occurrence of a cardiac tachyarrhythmia episode. Collection (i.e., acquisition and storage) of cardiac signal data and optionally other data only during time windows around episode occurrences may be useful in devices where memory is limited. Alternatively, if the system includes sufficient memory, cardiac signals may be continuously collected for later analysis to detect episode occurrences. Alternatively, the device may continuously or intermittently transmit the data in real time as it is acquired to a remote device.

The system may optionally have therapy capability. In therapy-capable implementations, the control processor 340 controls therapy circuitry such as pulse generator circuitry 330. The pulse generator circuitry 330 has the ability to generate pacing pulses for treating bradycardia and/or the ability to generate anti-tachyarrhythmia pacing pulses and/or high energy defibrillation or cardioversion shocks used for terminating dangerous tachyarrhythmias such as VF.

In various embodiments, the system acquires and stores cardiac signals sensed via the electrodes 305 continuously or during a time window before, during, and/or after cardiac tachyarrhythmia episodes or during other times, such as following LV or RV pacing. In one example, cardiac signals from each cardiac episode experienced by the patient are acquired along with one or more of cardiac marker channel signals. The signals associated with the episode are stored in the memory 345 and may be time and date stamped.

In one implementation, the cardiac electrodes 305, sense circuitry 310, memory 345, and control processor 340 are components of an implantable device, e.g., ICD 307. In this implementation, the episode data collected during one or more cardiac episodes may be transferred to a patient-external device 360 to facilitate interaction with a human analyst. For example, the ICD 370 may include a transmitter/receiver 350 configured to transmit the stored episode data to the patient-external device 370 automatically, periodically, or on command to a transmitter/receiver 362 of the patient-external device 360. In addition, data and/or program commands useful for controlling the operation of various components of the ICD 370 may be transmitted via the patient external device 360 and stored in the memory 345 of the ICD 370.

The patient external device 360, e.g., device programmer or remote server, optionally includes a tachyarrhythmia detector 364 configured to detect tachyarrhythmia episodes from the cardiac electrical signals downloaded from the ICD 370. The tachyarrhythmia detector 364 is further configured to determine characteristics of the tachyarrhythmia episodes from the electrogram signals. A data processor 366, optionally included in the patient external device 360, identifies episode types based on the morphological or interval characteristics of the tachyarrhythmia episodes. The number of different episode types into which the sensed tachyarrhythmia episodes are grouped may be determined algorithmically by the data processor 366, or may be input by a user. Although FIG. 3 illustrates the tachyarrhythmia detector 364 and data processor 366 as components of the patient-external device 360, alternatively, these functions could be implemented in the implanted device 370 or could be implemented partially in the implanted device 370 and partially in the patient external device 360.

Arrhythmia induction circuitry 390 is used to induce one more tachyarrhythmia episodes, such as during a pre-ablation procedure. Electrograms of the induced tachyarrhythmias are sensed via the cardiac electrodes 305 and sense circuitry 310. Features of the induced tachyarrhythmia episodes are compared to those of the identified episode types. If the features of an induced tachyarrhythmia episode are similar to the features associated with an identified episode type, then this information may be used by the electrophysiologist to inform the ablation process. For example, the electrophysiologist may be particularly interested in identifying cardiac sites that are responsible for episode types producing the greatest tachyarrhythmia burden. Ablation of these sites may be used to reduce or eliminates a most frequently occurring episode type or an episode type that is particularly problematic for the patient.

In some embodiments, the data processor 366 includes counter circuitry configured to count the number of tachyarrhythmia episodes for each episode type. The data processor 366 may optionally rank the episode types based on the number of tachyarrhythmia episodes counted for each episode type or based on other information. The count or rank of tachyarrhythmia episodes for each episode type and/or information related to similarity between induced tachyarrhythmia episode and identified episode types is transferred to a display device 368.

Figure 4:
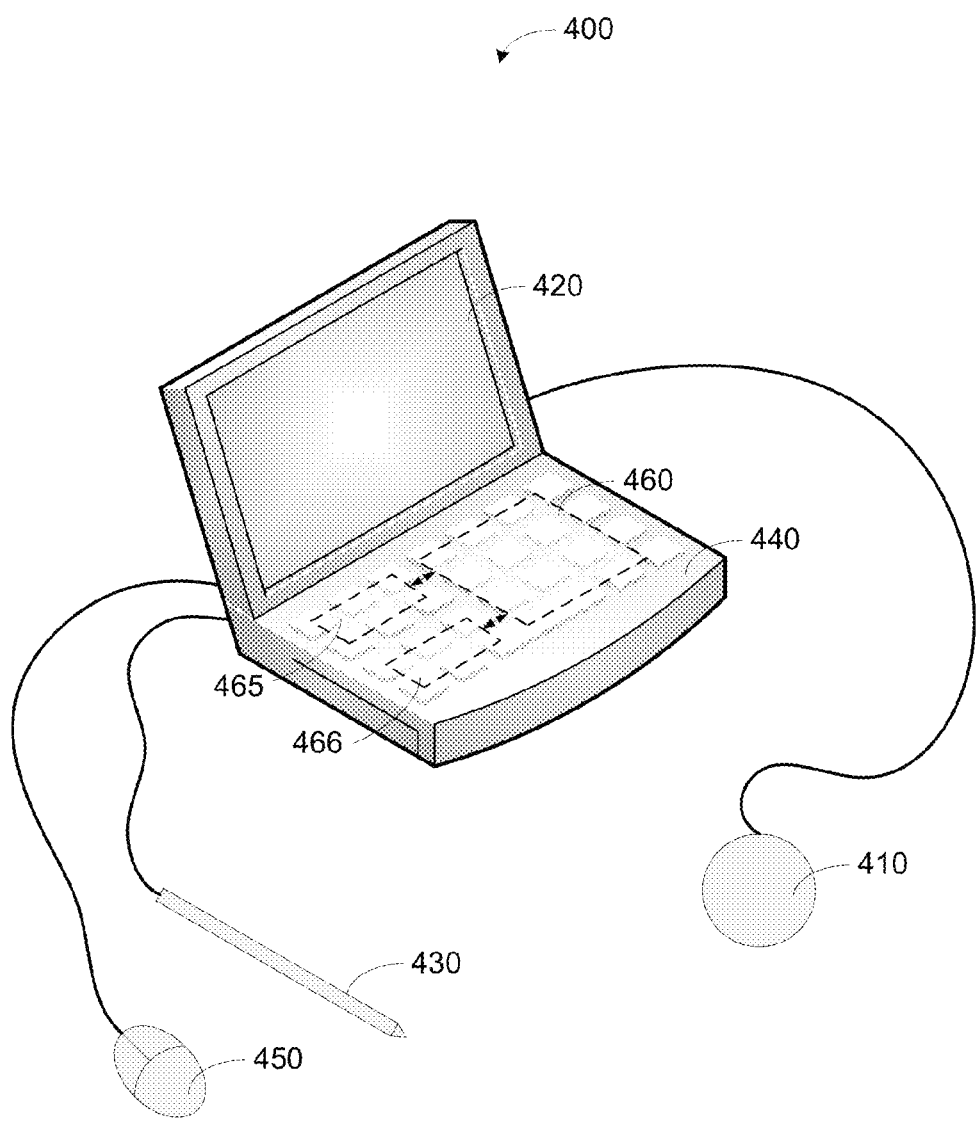
FIG. 4 is a diagram illustrating a patient-external device that provides a user interface allowing a human analyst to interact with the cardiac episode data in accordance with embodiments of the invention.

FIG. 4 illustrates a patient external device 400 that provides a user interface configured to allow a human analyst to interact with the episode data. The patient external device 400 is described as an ICD programmer, although the methods of the invention are operable on other types of devices as well, such as computers or patient information servers used in conjunction with a remote system, for example. The programmer 400 includes a programming head 410 which is placed over a patient's body near the implant site of an implanted device to establish a telemetry link between an ICD and the programmer 400. The telemetry link allows the cardiac episode data collected by the implantable device to be downloaded to the programmer 400. The downloaded cardiac episode data is stored in the programmer memory 465.

The programmer 400 includes a graphics display screen 420, e.g., LCD display screen, that is capable of displaying graphics, alphanumeric symbols, and/or other information. For example, the programmer 400 may graphically display one or more of the cardiac signals downloaded from the ICD on the screen 420. The display screen 420 may include touch-sensitive capability so that the user can input information or commands by touching the display screen 420 with a stylus 430 or the user's finger. Alternatively, or additionally, the user may input information or commands via a keyboard 440 or mouse 450.

The programmer 400 includes a data processor 460 including software and/or hardware for managing cardiac episode data stored in the memory 465 of the programmer 400. In one implementation, cardiac episode data is received from an ICD via communications circuitry 466 of the programmer 400. The data processor 460 identifies cardiac episode types based on one or more discriminating features of the tachyarrhythmia episodes detectable in the cardiac episode data. The data processor may compare features of induced tachyarrhythmia episodes to those of identified episode types. The tachyarrhythmia episodes associated with each episode types may be counted and/or ranked by the data processor as previously described. Information related to the comparison of induced tachyarrhythmia episodes to identified episode types, tachyarrhythmia episode count and/or rankings are presented to the user via a display screen 420.

In one embodiment, the data processor 460 may algorithmically group the stored tachyarrhythmia episodes having similar characteristics into episode types. The characteristics used for grouping the episode types may be identified by the user or may be identified by the data processor 460, for example.

In some embodiments, the groupings of similar episodes may be determined by a user and entered via the keyboard 420, the mouse 450, or stylus 430 for touch sensitive display applications. Methods and systems for grouping tachyarrhythmia episodes are described in U.S. Pat. No. 6,091,990 which is incorporated herein by reference.

In one embodiment, the data processor 460 or other remote patient-external device, processes tachyarrhythmia episode data stored in the ICD and downloaded to the remote device. The data processor 460 finds a tachyarrhythmia episode having a set of discriminating features, labels that episode as corresponding to an episode type and searches for additional episodes with discriminating features similar to the first episode type. If episodes having similar discriminating features are found in memory, the data processor 460 may count the number of similar episodes. The number of tachyarrhythmia episodes of a particular type may be displayed along with labels for the episode types on the programmer display 420.

ICDs are typically capable of acquiring cardiac EGM signals from multiple sensing vectors, including far field and near field sensing vectors. The morphological patterns present in the individual beat signals of a first tachyarrhythmia episode may be compared to the morphological patterns of a second one or more tachyarrhythmia episodes using information from both the far field and near field signals of the tachyarrhythmia episodes. In one implementation, the far field signal of a representative beat of the first tachyarrhythmia episode is aligned with the far field signal of a representative beat of a second tachyarrhythmia episode using fiducial points identified in the near field signals of the first and second tachyarrhythmia episode representative beats. After alignment, amplitude values of the representative beat signals are then compared to determine morphological similarity between the first and second tachyarrhythmia episodes.

Figure 5A:
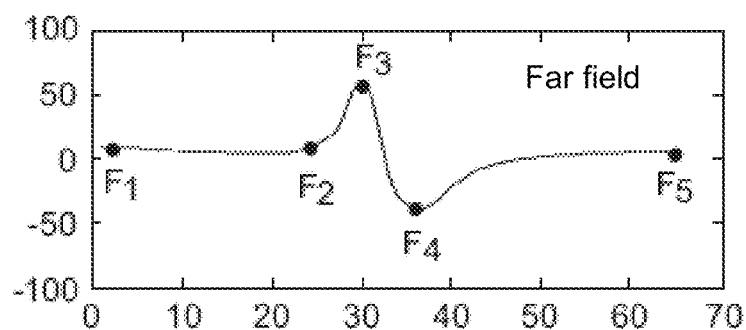
FIGS. 5A and 5B are diagrams illustrating near field and far field cardiac electrogram signals that may be used to identify cardiac tachyarrhythmia episodes in accordance with embodiments of the invention.
Figure 5B:
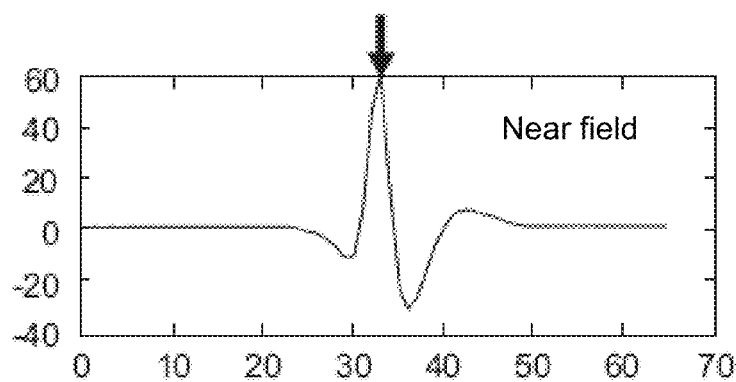

In one example, predetermined feature points $F_1$-$F_5$ may be extracted from a representative or composite far field signal beat of the first tachyarrhythmia episode as illustrated in FIG. 5A. After alignment using rate channel signals, illustrated in FIG. 5B, corresponding samples of the representative or composite beat of a second tachyarrhythmia episode are extracted and compared to the features of the first tachyarrhythmia episode. For example, the comparison may involve calculating a feature correlation coefficient (FCC) which quantifies the similarity between the signal morphology of the first and second tachyarrhythmia episodes. The FCC may be compared to a predetermined threshold to determine if morphology of the tachyarrhythmia episodes is similar or dissimilar.

Figure 6:
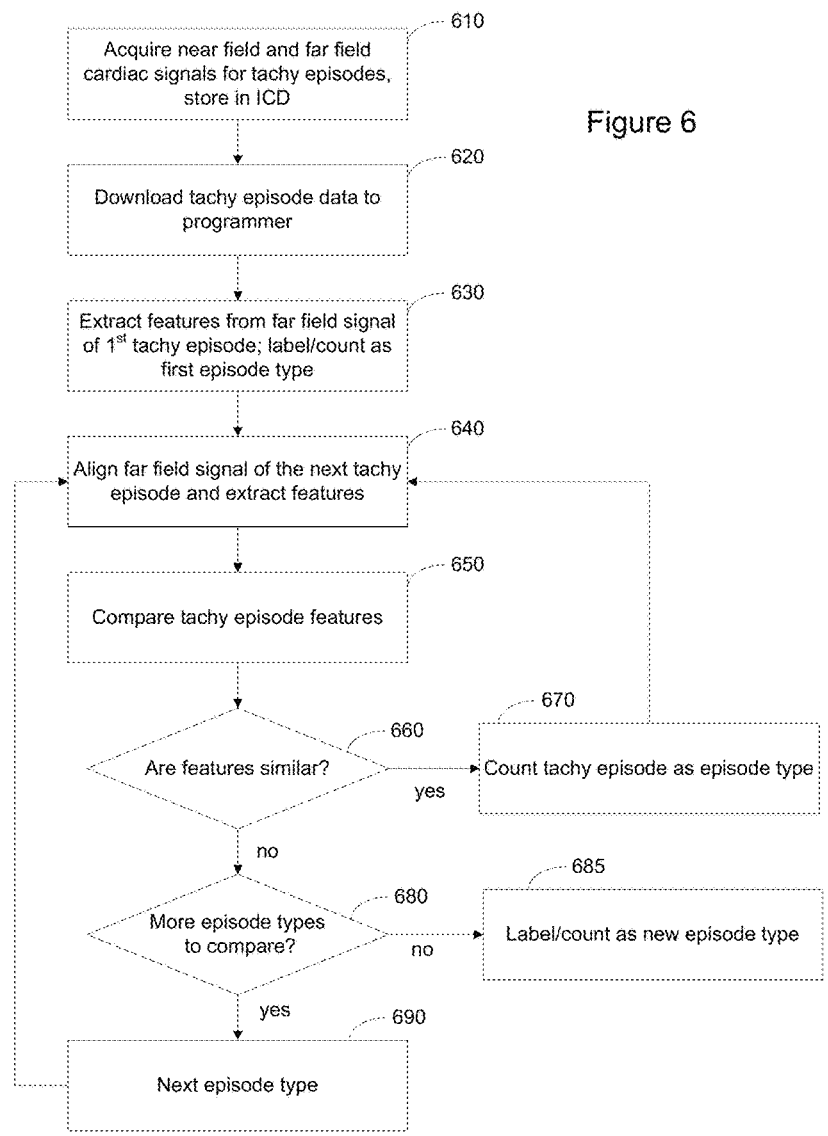
FIG. 6 is a diagram illustrating a process for labeling episode types and counting tachyarrhythmia episodes associated with the episode types based on near field and far field electrogram signals in accordance with embodiments of the invention.

The diagram of FIG. 6 illustrates a process for identifying episode types and counting tachyarrhythmia episodes associated with episode types in accordance with one embodiment. Near field and far field cardiac signals of tachyarrhythmia episodes are acquired and stored 610 in the ICD. For example, the near field signal may be acquired via a RV-tip to RV-ring sensing vector and the far field signal may be acquired via the SVC coil to can sensing vector.

The tachyarrhythmia episode signals are downloaded 620 to a device programmer or other remote patient-external computer. Features of the far field signal of a representative beat of a first tachyarrhythmia episode are extracted 630. The first tachyarrhythmia episode detected is labeled and counted as a new episode type. A next tachyarrhythmia episode is detected. A representative beat signal of the next tachyarrhythmia episode is aligned 640 with the representative beat of the first tachyarrhythmia episode using their corresponding rate channel fiducial points. The features of the far field signals of the tachyarrhythmia episodes are compared 650. If the features are similar 660, the next tachyarrhythmia episode is counted 670 as corresponding to the first episode type.

If the features of the next tachyarrhythmia episode are not similar 660 to the features of the first tachyarrhythmia episode, and there are more episode types to compare 680 to the tachyarrhythmia episode features, then the features of the tachyarrhythmia episode are compared to one or more additional episode types 690. If all the episode types have been compared to the tachyarrhythmia episode and none are similar, then the tachyarrhythmia episode is labeled and counted 685 as a new episode type. The process illustrated in the diagram of FIG. 6 continues until all tachyarrhythmia episodes have been counted.

While the labeling and counting process described in connection with FIG. 6 can be accomplished using sensing vectors available via a single RV lead, a more precise characterization of tachyarrhythmia episode types may be possible through the use of sensing vectors of multiple leads available in biventricular ICD systems. The process described in connection with FIG. 6 above may be based on a single sensed near field electrogram occurring within a single sensed far-field electrogram. With the addition of an LV lead, as in the case of a biventricular ICD, the available electrogram signals are expanded to left and right near field electrogram signals occurring in conjunction with multiple far-field electrograms. For example, additional sensing vectors available from a biventricular device include the vectors in the representative list provided in Table 1:

TABLE 1

| ANODE | CATHODE |
| --- | --- |
| SVC Coil | RV coil (or ring), RV tip, LV ring, or LV tip |
| Can | RV coil (or ring), RV tip, LV ring, or LV tip |
| RV coil | LV coil and LV tip |
| RV tip | LV coil and LV tip |

The use of a multiple lead recording system for tachyarrhythmia episodes provides information that may be used to determine a more precise characterization of all tachyarrhythmias.

Figure 7:
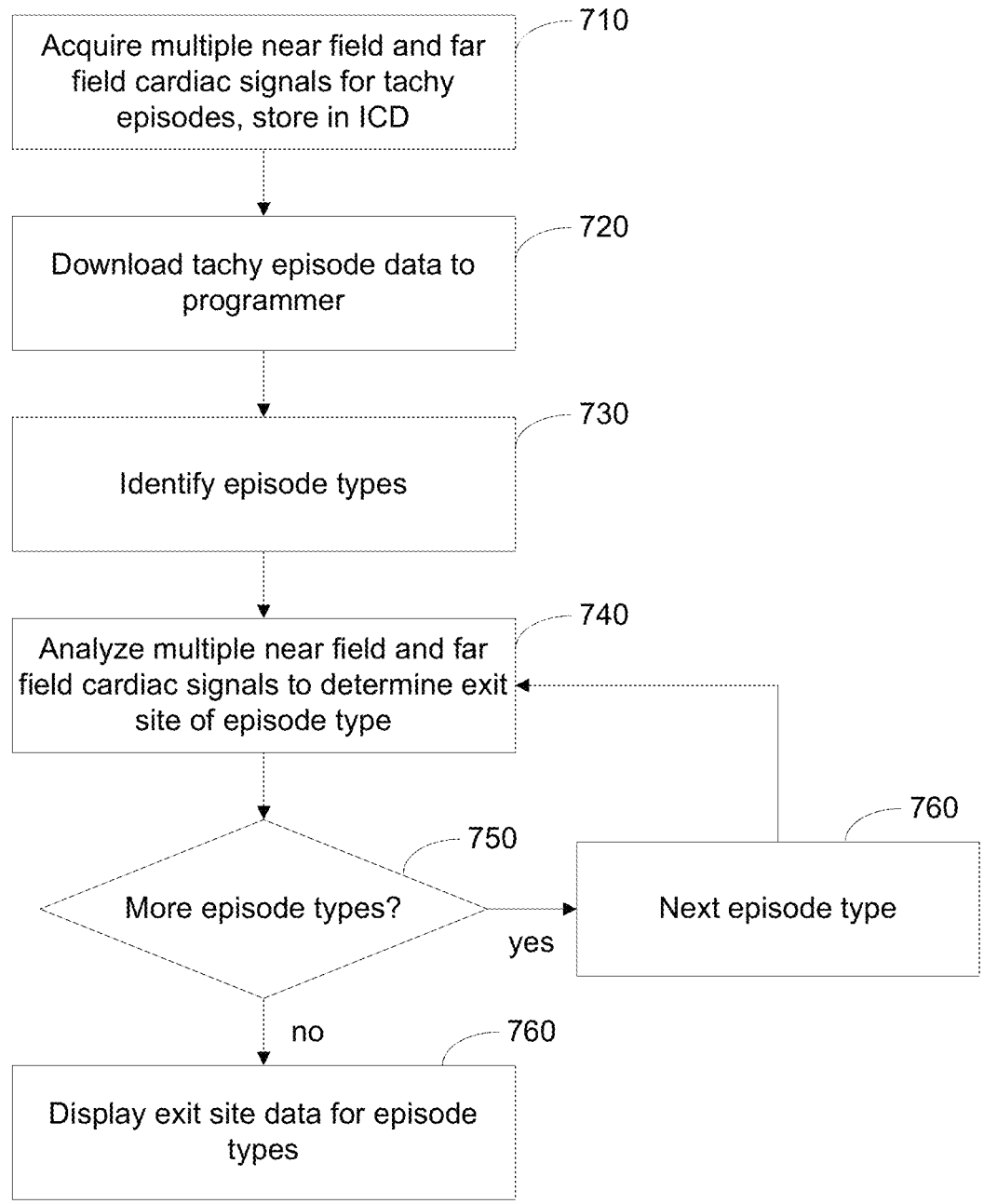
FIG. 7 is diagram illustrating a process for determining exit sites for various tachyarrhythmia episode types in accordance with embodiments of the invention.

Analysis of the electrogram signals of a multi-lead ICD may also be performed to indicate exit sites of the various episode types in the same way that analysis of a 12-lead electrocardiogram can identify a PVC or VT site of origin to a region of the heart. Analysis of the vector on a far-field EGM could regionalize the site of origin of the PVC or VT to a specific location in either the left or right ventricle. In one embodiment of the invention, EGM signals acquired from the sensing vectors of a multi-lead biventricular ICD are analyzed to determine exit sites for each of episode type. A process for determining exit sites for one or more episodes types is illustrated by the diagram of FIG. 7. Multiple near field and far field electrogram signals of tachyarrhythmia episodes are acquired and stored 710 by an ICD. Periodically or on command, the EGM data are downloaded 720 to a device programmer or other remote, patient-external device. The episode types are identified 730 as previously described. For each episode type, the multiple EGM signals are analyzed 740 to determine an exit site of the episode type. This process continues 750 until the exit site for each identified episode type has been analyzed 760. The exit site information is displayed 770, optionally along with additional information including the episode type labels a number of tachyarrhythmia episodes detected for each episode type and/or rankings of the episode types.

Location of PVC or VT exit site, e.g., lateral wall, apex, or non-septal site may be characterized by distinct patterns when compared to LV pacing, RV pacing and sinus rhythm. For example, if a particular episode type morphology resembles LV pacing, the exit site for that episode type can be assumed to be near the LV pacing site. The process described above may be modified to alternatively or additionally include analysis of signals produced by LV pacing, RV pacing, and sinus rhythm to determine the exit site for the tachyarrhythmias.

In accordance with various embodiments, the number of episode types is algorithmically determined. For example, the episodes may be clustered using a genetic algorithm, such as a K-means clustering algorithm. In one embodiment involving K-means clustering, each episode's N distinguishing features are expressed as an N-dimensional feature vector. The feature vectors of all episodes can be thought of as being plotted in N-dimensional space. Episodes similar in conduction pattern will be plotted close to each other while episodes having different in conduction pattern will be plotted farther from each other. The K-means clustering algorithm will automatically cluster the episodes into K groups, with each group represented by its mean feature vector and each episode assigned to the group with the closest mean feature vector.

In some embodiments, groups may be formed where a particular episode can be a member of only one group. In other embodiments, a particular episode may be a member in more than one group. For example, a fuzzy K-means clustering algorithm may be used to group the episodes. With conventional K-means clustering described above, an episode can belong to only one cluster as the conventional algorithm assigns to an episode one crisp membership value per cluster (equal to 0 if the episode is not a member of the cluster and 1 if the episode is a member of the cluster). In contrast, with the fuzzy algorithm, an episode can belong to several clusters, as the fuzzy algorithm assigns to an episode one membership value per cluster ranging from 0 to 1. These membership values specify the episode's degree of membership into each cluster.

Note that in the above-described embodiments, the number of clusters is first determined before using the genetic K-means algorithm to cluster the episodes. In some implementations, the physician specifies K which is the number of groups or clusters. In other implementations, the processor uses a predetermined number as K. In yet other implementations, the processor determines the value of K by partitioning the N-dimensional space based upon the density of the feature vectors in the space. In a further implementation, the processor determines the value of K by partitioning the N-dimensional space based upon a matrix of similarity measurements comparing each feature vector to each other.

In one scenario, the processor may use a probability function such as a probability density function (PDF) or a cumulative distribution function (CDF) to determine the number of clusters. This technique is described with reference to determining the number of rate zones in commonly owned U.S. Pat. No. 7,580,741 which is incorporated herein by reference. The same principle is applicable to determining the number of clusters based on the PDF or CDF formed using discriminating features or mean feature vectors of the episodes. The number of groups may be determined from the morphology of the CDF or PDF as is described for determining the number of rate zones in the previously incorporated patent application.

In yet other embodiments, the episodes are first ordered and are then grouped. For example, the episodes may first be ordered based on the value of one discriminating feature or may be ordered based on N discriminating features. A physician may identify groups of the ordered episodes. In one scenario, the physician may identify episodes, denoted herein as border episodes. The border episodes may have one or more discriminating features that appear to form a natural division between one group and another group, for example. After determination of the number of episode types, counting and/or ranking the episode types may proceed as described above.

As the amount of information collected and stored in ICDs increases, the interpretation of data becomes more complex and time consuming. The present invention provides methods and systems for arranging cardiac episodes based on discriminating features of the episode data. The processes described herein allow a physician to more easily identify cardiac episodes types and determine the VT burden associated with different episode types. The methods of the present invention allow a physician to identify the number and/or frequency of different types of cardiac episodes experienced by the patient. Data processing algorithms used to identify episode types, count tachyarrhythmia episodes associated with episode types and rank episode types to determine the VT burden of the various episode types may operate in an implantable or patient-external device that also acquires the episode data. In another version, an implantable or non-implantable device may acquire the episode data and the arrangement and/or labeling of the data may be performed by a device programmer or a remote server, for example.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A cardiac system, comprising:
    an implantable sensing system configured to sense first electrogram signals during a first period of time and to sense second electrogram signals during a second period of time;
    a tachyarrhythmia detector configured to detect intrinsic tachyarrhythmia episodes using the first electrogram signals and to detect an induced tachyarrhythmia episode using the second electrogram signals;
    a data processor configured to:
        identify intrinsic tachyarrhythmia episode types based on a comparison of morphological characteristics extracted from the first electrogram signals with morphological characteristics extracted from the second electrogram signals of the induced tachyarrhythmia episode that determines a similarity between the induced tachyarrhythmia episode and at least one intrinsic tachyarrhythmia episode type;
        determine a tachyarrhythmia burden for each of the identified intrinsic tachyarrhythmia episode types; and
        rank each of the identified intrinsic tachyarrhythmia episode types based on each of the associated tachyarrhythmia burdens; and
    a display configured to present information related to the similarity between the induced tachyarrhythmia episode and the at least one intrinsic tachyarrhythmia episode type.

2. The system of claim 1, wherein each of the tachyarrhythmia burdens is based on information about each of the associated intrinsic tachyarrhythmia episode types, the information including one or more of information defining number of occurrences, frequency of occurrences, instability, morphological disorganization, tendency to accelerate to ventricular fibrillation, and responsiveness to treatment.

3. The system of claim 1, wherein the data processor is configured to identify the intrinsic tachyarrhythmia episode types based on morphological characteristics of the first electrogram signals.

4. The system of claim 1, wherein data processor is configured to identify the intrinsic tachyarrhythmia episode types based on one or both of P-R or R-P timing intervals of the first electrogram signals that are compared to the second electrogram signals.

5. The system of claim 1, wherein data processor is configured to identify the intrinsic tachyarrhythmia episode types based on one or both of Fourier analysis and wavelet analysis of the first electrogram signals.

6. The system of claim 1, wherein the data processor is further configured to determine an exit site of one or more of the intrinsic tachyarrhythmia episode types.

7. The system of claim 1, further comprising a pulse generator configured to deliver pacing pulses to induce the induced tachyarrhythmia episode.

8. The system of claim 1, wherein the implantable sensing system includes electrodes disposed in or on left and right ventricles and the first electrogram signals are sensed using the electrodes disposed in or on the left and right ventricles.

9. The system of claim 8, wherein the data processor is further configured to analyze the first electrogram signals sensed using the electrodes disposed in or on the left and right ventricles to determine exit sites of the intrinsic tachyarrhythmia episode types.

10. The system of claim 1, further comprising a pulse generator configured to deliver pacing pulses to induce the induced tachyarrhythmia episode.

11. A cardiac system, comprising:
an implantable sensing system configured to sense first electrogram signals during a first period of time and to sense second electrogram signals during a second period of time;
a tachyarrhythmia detector configured to detect intrinsic tachyarrhythmia episodes using the first electrogram signals and to detect an induced tachyarrhythmia episode using the second electrogram signals;
a data processor configured to:
identify intrinsic tachyarrhythmia episode types based on a comparison of morphological characteristics extracted from the first electrogram signals with morphological characteristics extracted from the second electrogram signals of the induced tachyarrhythmia episode that determines a similarity between the induced tachyarrhythmia episode and at least one intrinsic tachyarrhythmia episode type;
determine a tachyarrhythmia burden for each of the identified intrinsic tachyarrhythmia episode types;
rank each of the identified intrinsic tachyarrhythmia episode types based on each of the associated tachyarrhythmia burdens; and
determine an exit site for each of the identified intrinsic tachyarrhythmia episode types; and
a display configured to present information related to the identified intrinsic tachyarrhythmia episode types and exit sites.

12. The system of claim 11, wherein the display is configured to present information related to the similarity between the induced tachyarrhythmia episode and the at least one intrinsic tachyarrhythmia episode type.

13. The system of claim 11, wherein the display is configured to present information related to the rankings of the episode types.

14. The system of claim 11, wherein the tachyarrhythmia burden is based on information about the associated intrinsic tachyarrhythmia episode type including one or more of number of occurrences, frequency of occurrences, instability, morphological disorganization, tendency to accelerate to ventricular fibrillation, and responsiveness to treatment.

15. The system of claim 11, wherein the data processor is configured to identify the intrinsic tachyarrhythmia episode types based on morphological characteristics of the first electrogram signals.

16. The system of claim 11, wherein the data processor is configured to identify the intrinsic tachyarrhythmia episode types based on:
one or both of P-R timing or R-P timing intervals of the first electrogram signals; or
one or both of Fourier analysis and wavelet analysis of the first electrogram signals.

17. The system of claim 11, wherein the data processor is configured to discriminate a first type of ventricular tachyarrhythmia episode from a plurality of ventricular tachyarrhythmia episode types.

18. The system of claim 11, wherein the implantable sensing system includes electrodes disposed in or on left and right ventricles and the first electrogram signals are sensed using the electrodes disposed in or on the left and right ventricles.

19. The system of claim 18, wherein the data processor is further configured to analyze the first electrogram signals sensed using the electrodes disposed in or on the left and right ventricles and determine the exit sites of the intrinsic tachyarrhythmia episode types.

* * * * *